United States Patent [19]

Takeuchi

[11] 3,991,365

[45] Nov. 9, 1976

[54] INSTANTANEOUS FREQUENCY MEASUREMENT SYSTEM

[75] Inventor: Yasuhito Takeuchi, Kunitachi, Japan

[73] Assignee: Hewlett-Packard Company, Palo Alto, Calif.

[22] Filed: Oct. 22, 1975

[21] Appl. No.: 624,680

[30] Foreign Application Priority Data
Oct. 31, 1974  Japan.............................. 49-125915

[52] U.S. Cl. ........................ 324/78 R; 128/2.05 T; 128/2.05 Z; 324/77 G; 73/194 A
[51] Int. Cl.² .......................................... G01R 23/02
[58] Field of Search.................. 128/2.05 T, 2.05 Z, 128/2.06 F; 340/3 D; 73/69, 67.5, 194 A; 324/78 R, 78 D, 77 G

[56] References Cited
UNITED STATES PATENTS

| 3,813,654 | 5/1974 | Clifton | 128/2.05 T |
|---|---|---|---|
| 3,934,577 | 1/1976 | Romani | 128/2.05 T |

*Primary Examiner*—R. V. Rolinec
*Assistant Examiner*—Michael J. Tokar
*Attorney, Agent, or Firm*—Stephen P. Fox; Robert S. Hulse

[57] ABSTRACT

This invention relates to a system for measuring in real time, by auto-correlation, the period and frequency of a periodic biomedical source signal with random components such as an ultrasound doppler fetal heart beat signal.

Before and during delivery of a fetus, the invention enables an obstetrician to continuously monitor and record the heart rate of the fetus in real time.

10 Claims, 13 Drawing Figures

INSTANTANEOUS FREQUENCY MEASUREMENT SYSTEM

BACKGROUND OF THE INVENTION

Typically, fetal signals that are available for measurement include direct or vaginal fetal ECG signals, indirect or abdominal fetal ECG signals, fetal phonocardiographic signals, and ultrasound doppler fetal heart beat signals. Of these fetal signals, ultrasound doppler fetal heart beat signals seem best suited for clinical applications because they can be obtained non-invasively, without harm to mother or fetus, any time from about 10 weeks of pregnancy until delivery, and further because these signals have an acceptable signal to noise ratio and are not adversely affected by obesity of the mother, movement of the mother, fetal position, or ambient and acoustic noises.

Heretofore, the method of measuring fetal heart rate from an ultrasound doppler fetal heart beat signal required the recognition of a suitable component of the signal, the generation of a trigger pulse having a predetermined temporal relationship to said component, the measuring of the period between trigger pulses, and the calculation of the reciprocal value of said period.

Because an ultrasound doppler fetal heart beat signal includes blood flow, muscle, and valve signals as components of the heart beat signal, and because the envelope of the valve signal component is typically suited for triggering, this valve signal component has often been used as trigger signals. However, because there is more than one valve signal in an ultrasound doppler fetal heart beat signal, and because it is difficult to get a reliable signal because the level of these signals fade from time to time, the use of valve signals as trigger signals often produces ambiguous and incorrect results.

SUMMARY OF THE INVENTION

According to the illustrated embodiment of the present invention, a real time auto-correlation heart rate meter is provided for analyzing ultrasound doppler fetal heart beat signals. This meter includes a pre-processor having band pass filters (BPF), automatic level control (ALC), envelope detector and the like for providing triggering signals, and includes an auto-correlator, a period or fundamental peak detector, and a period-to-heart-rate converter. The auto-correlation function is performed in real time, within substantially one period of the source signal.

DESCRIPTION OF THE PREFERRED EMBODIMENT

Figure 1:
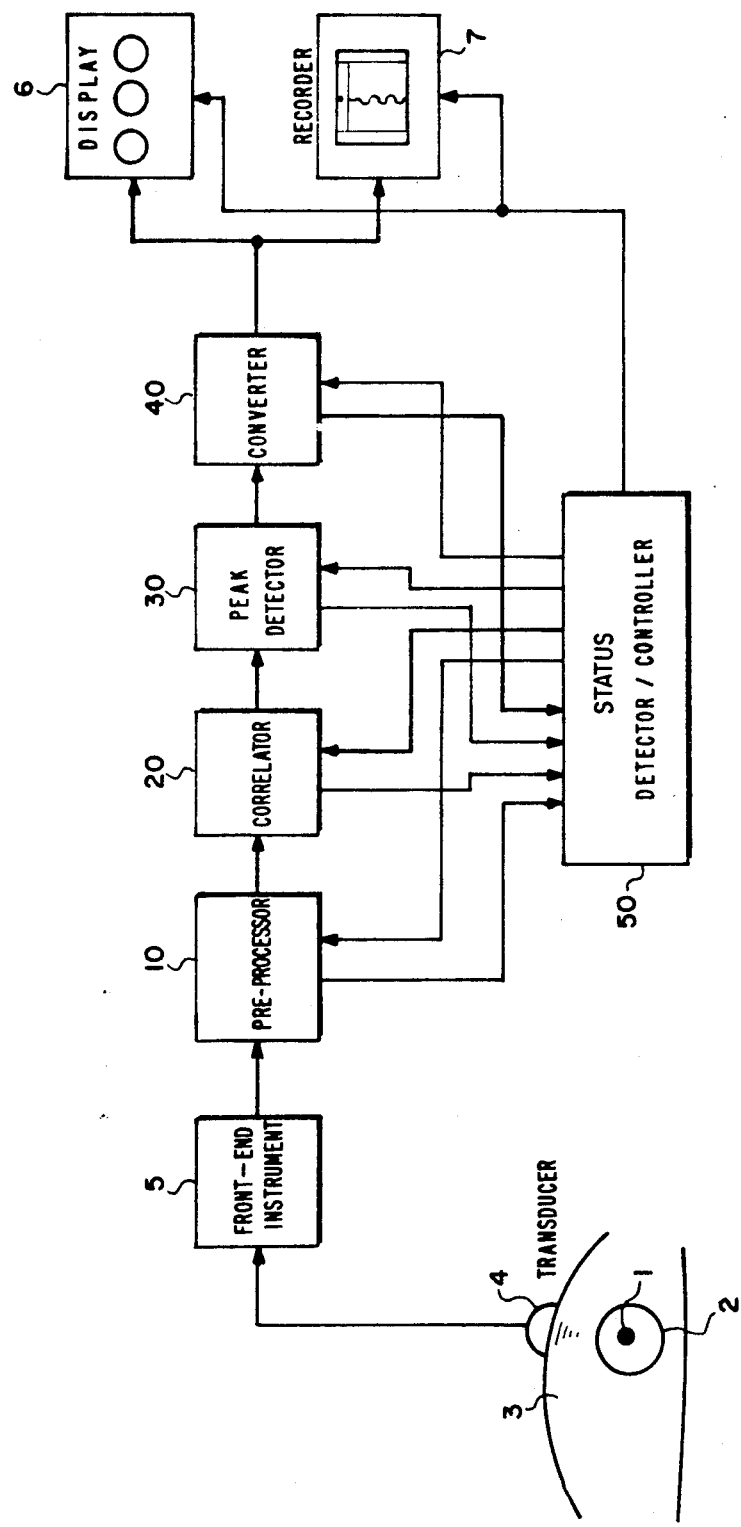
FIG. 1 is a block diagram of the system of the present invention.

FIG. 1 is a block diagram of an ultrasound doppler fetal heart rate meter according to the preferred embodiment of the present invention. Signal from a fetal heart 1 shown in a mother 3 is picked up by an ultrasound doppler transducer 4 and applied to a pre-processor 10 via a front-end instrument 5. This pre-processor 10 filters out blood flow signal component and allows the fetal heart signal with valve and muscle signal components to be processed for input to correlator 20.

Block 30 represents a fundamental-peak detector which searches the output of correlator 20 for a fundamental peak, and block 40 represents a peak-location to fetal-heart-rate converter for calculating fetal heart rate from peak-location detected by peak detector 30.

Block 50 represents a status detector/controller, which detects the status of blocks 10–40 and controls the functions of said blocks according to their status. The output of converter 40 is applied to display element 6 for the purpose of displaying the fetal heart rate, and to recorder 7 to produce a fetal heart rate record. Display 6 and recorder 7 are also controlled by status detector/controller 50.

Figure 2:
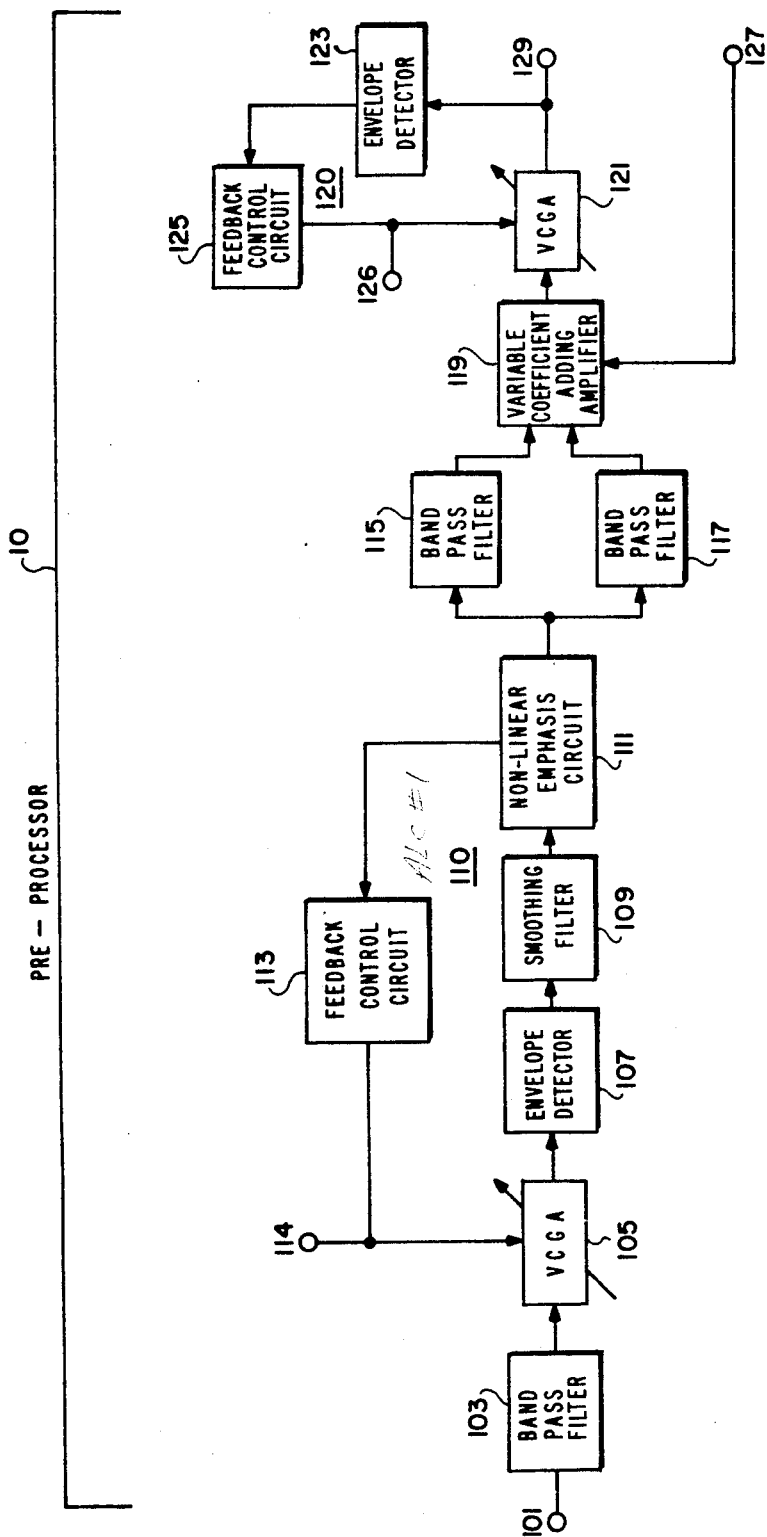
FIG. 2 is a block diagram illustrating the components of the pre-processor of FIG. 1.

FIG. 2 is a block diagram of pre-processor 10 in greater detail. Block 103 represents a band pass filter of about 300–1000 Hz used to filter out blood flow signal contained in the input signal applied to terminal 101 of the pre-processor 10. The filter 103 allows the input signal with heart valve and muscle signal components to pass to voltage control gain amplifier 105. Voltage control gain amplifier (VCGA) 105 in series with envelope detector 107, smoothing filter 109, non-linear emphasis circuit 111, and feed back circuit 113 form 1st automatic level control (ALC) 110. The VCGA 105, which may be an operational amplifier fed back by an LED-controlled cadmium sulfide photoconductor cell, produces essentially a negative exponential function of the applied signal current.

The output of the VCGA 105 is then rectified by envelope detector 107 and smoothed by smoothing filter 109 to eliminate audio frequency components. A low-pass filter having cut-off frequency of 50–70 Hz may be a suitable smoothing filter 109. The non-linear emphasis circuit 111, like a quasi-logalithmic converter, expands the low level portion of the input signal, and compresses the high level portion. The output of this non-linear emphasis circuit 111 is also used as a control parameter for first ALC loop 110, this output being proportional to the db value of the input signal level. The feed back time constant elements of the loop 110 operate in their nonsaturated areas, and provide a constant response characteristic for any input signal level, thereby producing little interference from spiky noises or from high level noises with short durations. The effective time constant of this first ALC loop 110 is approximately 1.5–2.2 seconds, sufficient to conserve the input signal envelope for any period of fetal heart beat, and to compensate for any level changing that may occur during such beats.

The output of non-linear emphasis circuit 111 is applied to band pass filters 115 and 117, and the outputs of these filters 115, 117 are applied to and combined by variable coefficient adding amplifier 119. This causes the suppression of the fundamental frequency component of fetal heart beat, which has a frequency range of from 0.8 to 3.5 Hz or 48–212 beats per minute. Band pass filter 115 has a pass band of about 15–50 Hz, and band pass filter 117 has a pass band of about 3.3–15 Hz. The mixing ratio of signals applied to adding amplifier 119 is controlled by status detector/controller 50 via terminal 127. Status detector/controller 50 is described subsequently herein. The output from the variable coefficient adding amplifier 119 is a composite envelope signal which is fed into a second ALC loop 120. Loop 120, which comprises a VCGA 121, an envelope detector 123, and a feed back circuit 125 similar to first ALC loop 110, produces a constant level signal at output terminal 129.

Thus, signal pre-processor 10 produces a constant level composite envelope signal at its output terminal 129 for varying input signal levels applied to input terminal 101.

Figure 3:
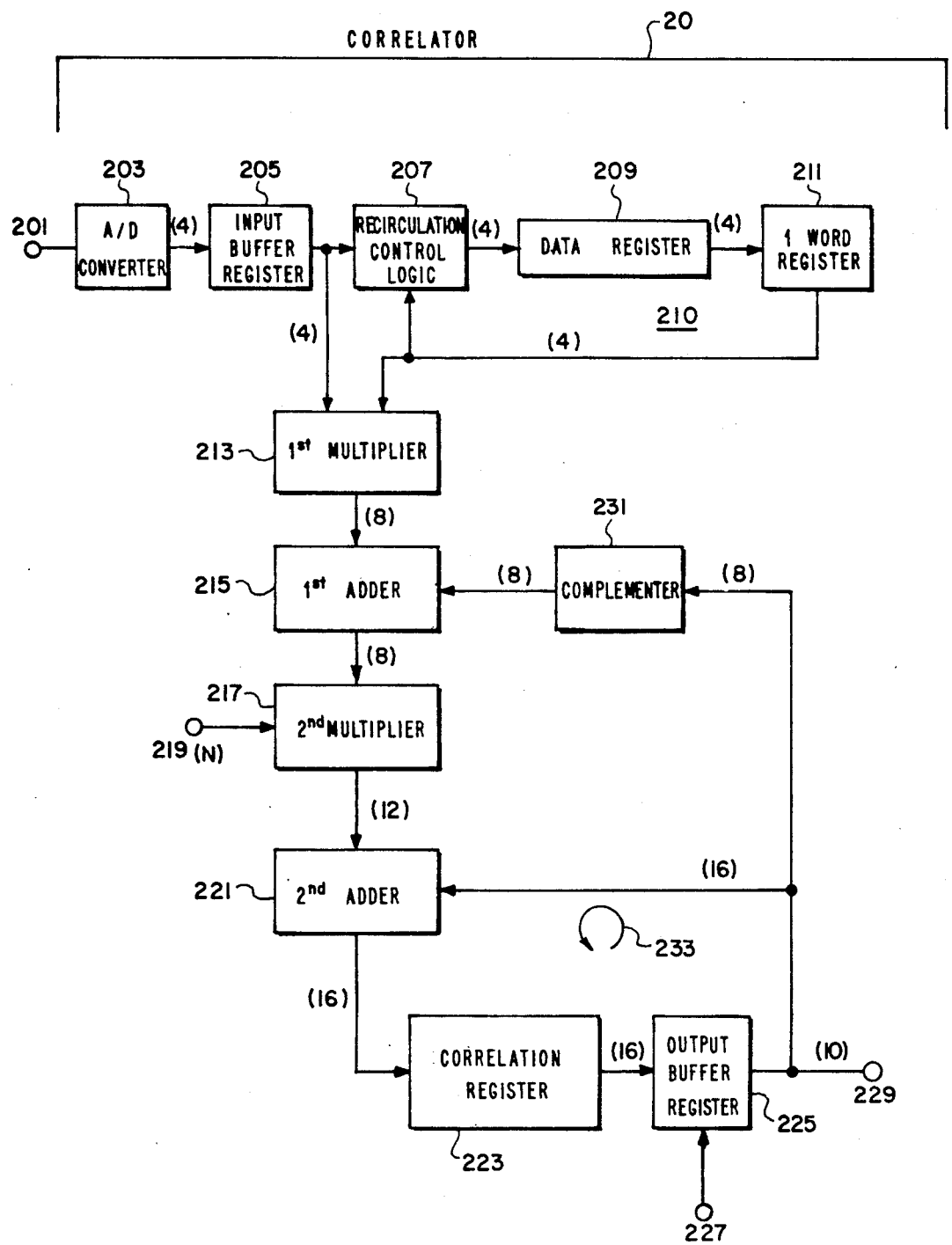
FIG. 3 is a block diagram illustrating the components of the correlator of FIG. 1.

FIG. 3 is a detailed block diagram of the correlator 20, showing signal flow. Analog-to-digital (A–D) converter 203 converts to 4-bit digital form the input signal applied to terminal 201 from output terminal 129. The digital form, one sign bit and 3 magnitude bits, is expressed in 2's complement binary form.

The output of A–D converter 203 is stored in input-buffer register 205 and applied to first multiplier 213 and to data register 209 via recirculation control logic 207. Data register 209 is a 256 word shift register, each word containing 4 bits of data. Each word of this data is circulated, via register 211, in storage loop 210. A circular shift of all 256 words is equivalent to one recirculating period of the loop 210. When new data is introduced, it is stored in the data register 209 at the word containing the oldest data value recirculating back from register 211, and register 211 is made to contain the next oldest data value. A data sampling rate is 5 mseconds (200 Hz) is selected equal to one recirculation period of loop 210, or 256 data shift steps.

The first multiplier 213 produces a product of the contents of register 211 and input buffer register 205. The contents of buffer register 205 is updated with newly sampled data each 5 mseconds. The output of first multiplier 213 is equal to the following produce $P_{(n,k)}$ at the $k$th step of the $n$th recirculation period:

$$P_{(n,k)} = D_n \times D_{(n-k)} \qquad (1)$$

where $D_{(n-k)}$ represents data sampled at the $(n-k)$th recirculation period and $D_n$ represents data sampled at the $n$th recirculation period, $k$ being less than $n$.

If the products $P_{(n,k)}$ are summed over the range of $n$ values for each $k$, an auto-correlation value would be formed according to each $k$. If all such $P_{(n,k)}$ values were stored for a typical period, extensive memory storage facilities would be required.

Correlator 20 obviates the need for extensive storage by utilizing exponential mode integration as described following. The output from first multiplier 213 and the twos complement of a previous correlation value accumulated in correlation register 223 are applied to first adder 215 via output buffer register 225 and complementer 231. First adder 215 sums these values as follows:

$$S_{(n,k)} = P_{(n,k)} - C_{(n,k)} \qquad (2)$$

where $c$ represents the auto-correlation and $S$ represents an intermediate sum. This intermediate sum $S_{(n,k)}$ is then applied to second multiplier 217 which, under control of status detector/controller 50 via terminal 219, multiplies the intermediate sum by constant $\frac{1}{2}^N$ which is equivalent to dividing said sum by $2^N$; the value of N is described hereinafter. Next, the output of second multiplier 217 together with the previous correlation value from register 223, via buffer register 225, are applied to second adder 221. This adder 221 together with correlation register 223 and buffer register 225 constitute recirculation loop 233, which operates synchronously with the data register loop 210. Loop 233 accumulates a current correlation value in register 223 according to the following equation:

$$C_{(n+1,k)} = C_{(n,k)} + \frac{1}{2^N}\left\{P_{(n,k)} - C_{(n,k)}\right\}$$
$$= \left\{1 - \frac{1}{2^N}\right\}C_{(n,k)} + \frac{1}{2^N}\left\{D_n \cdot D_{(n-k)}\right\} \qquad (3)$$

Old correlation values are replaced and new correlation values are formed at a constant rate determined by N.

This replacement or decaying of old values is analagous to a capacitor-resistor decay time constant representable by an exponential function as follows when the equation (3) is summed:

$$C_{(n,k)} = \frac{1}{2^N} \sum_{m=0}^{\infty} (1 - \frac{1}{2^N})^m \cdot \left\{D_{(n-m)} \cdot D_{(n-m-k)}\right\} \qquad (4)$$

where the term $$(1 - \frac{1}{2^N})^m$$

represents a digital expression of an exponential function. The equation (4) corresponds to the following analog expression of a weighted auto-correlation function:

$$F_{u_0, \tau} = \frac{1}{\alpha} \int_{t=t_0}^{-\infty} \exp\left\{-\frac{t}{\alpha}\right\} f(t) \cdot f(t-\tau) dt \qquad (5)$$

where
  F represents the auto-correlation,
  $f$ represents source signal function,
  $\alpha$ represents data length, determined by a decay constant,
  $t_0$ represents current or real time,
  $t$ represents integration variable,
  $\tau$ represents time delay or deviation.

From the above, it can be seen that the equivalent or effective data length (i.e., the amount of data sufficient to calculate the auto-correlation) is determined by N or $\alpha$, not by the actual amount of data received for computation, nor by the values of $k$ or $\tau$. A person can control data length by changing $\alpha$ or N and applying this N or $\alpha$ value to terminal 219. The relationships between $\alpha$, N, $T_{eq}$, and $m_{eq}$ are as follows:

$$T_{eq} = \alpha = m_{eq} \times (5 \text{ mseconds}) \quad (6)$$

and from formula (4), $$m_{eq} = - \frac{1}{\ln(1 - \frac{1}{2^N})} \quad (7a)$$

or, $$N = -\log_2 \left\{ 1 - \exp\left(-\frac{1}{m}\right) \right\} \quad (7b)$$

for N very much larger than 2, $$m_{eq} \approx 2^N \quad (8a)$$

or, $$N \approx \log_2 m \quad (8b)$$

for example, when N = 5 to 9, $m_{eq}$ and $T_{eq}$ have the following values:

| N | $m_{eq}$ | $T_{eq}$ |
|---|----------|----------|
| 5 | 31.4974 | 157.5 mseconds |
| 6 | 63.4987 | 317.5 mseconds |
| 7 | 127.4993 | 637.5 mseconds |
| 8 | 255.4997 | 1.277 mseconds |
| 9 | 511.4998 | 2.557 mseconds |

Therefore, an appropriate N for applying to a fetal heart cycle period, which is typically 283–1,250 mseconds, equivalent to 48–212 beats per minute, is 6, 7, or 8. N need not be a fixed value, but may be varied according to the heart period at a given time. Complete correlation values accumulated for each 5 msecond data cycle are output at terminal 229. Reset input terminal 227 of output buffer 225 is used to clear the contents of correlation register 223.

Figure 4:
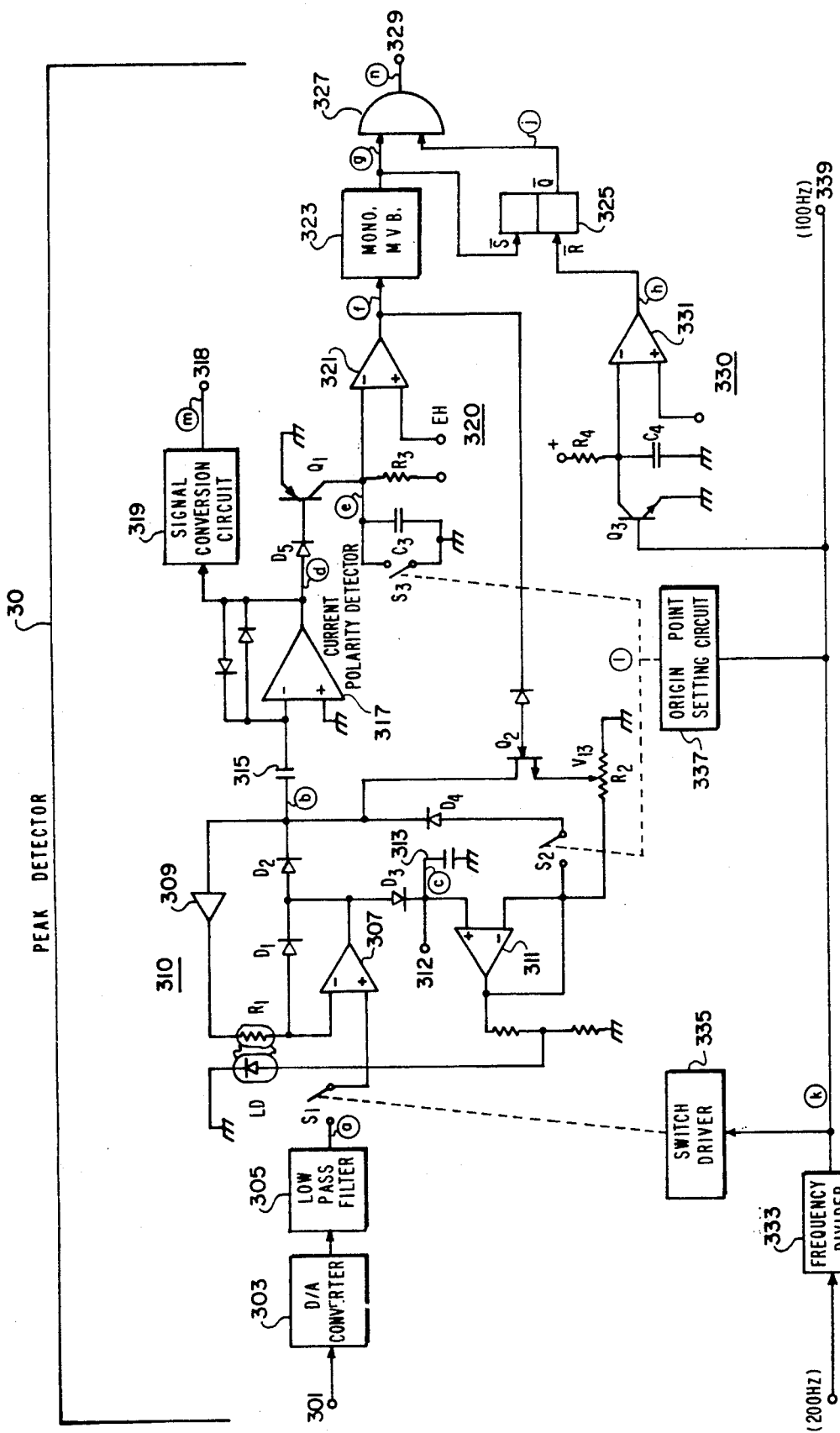
FIG. 4 is a combined block and schematic diagram illustrating the components of the peak detector of FIG. 1.
Figure 5:
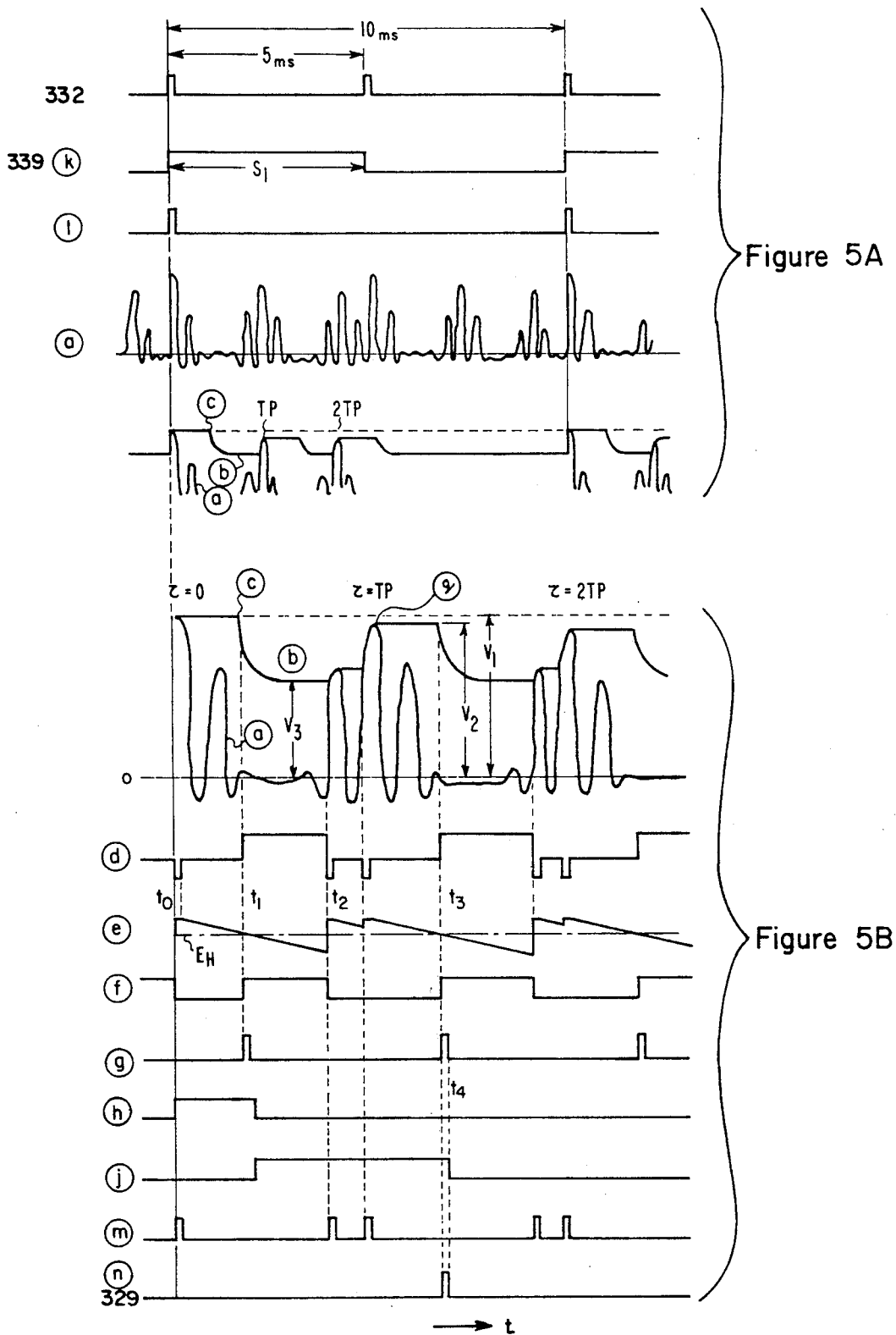
FIGS. 5A and 5B are waveform and timing diagrams illustrating signals available at selected points of the peak detector of FIG. 4.

FIG. 4 shows the components of peak detector 30. FIG. 5 shows the waveforms of signals at selected points (a), (b), (c), (d), (e), (f), (g), (h), (j), (k), (l), (m), and (n) of FIG. 4. The output from terminal 229 (FIG. 3) is applied to digital-to-analog converter (DAC) 303 (FIG. 4), which is a 10-bit 2's complement converter, and the output from DAC 303, which is a step function, is smoothed by low pass filter 305. The output of low pass filter 305 is a continuous function signal (a) (FIGS. 5A and 5B).

Flip-flop 333 divides the recirculation frequency (200 Hz) into half (100 Hz), and this 100 Hz frequency is used to drive switch S1 by means of driver circuit 335. This causes third ALC amplifier 310 to accept the output from filter 305 at each odd numbered recirculation cycle, and not at each even numbered cycle. In the third ALC circuit 310, operational amplifier 307 applies a peak output signal to hold capacitors 313 and 315, and to buffer amplifier 309. The output from amplifier 309 is fed back to amplifier 307 via feed back-control resistor element R1. Resistor R1 is photocoupled to an LED (LD) which is controlled by gain control amplifier 311.

First hold capacitor 315 is virtually grounded, being connected to current polarity detector (amplifier) 317. Second hold capacitor 313 is directly grounded. Both capacitors 313 and 315 have the same voltage when the input voltage is increased, and because of diodes D2 and D3, they are not discharged when the voltage decreases.

Second hold capacitor 313 has a discharge time constant longer than the repetition rate (10 mseconds) of the applied signal (c) but shorter than the heart beat period which is, typically, at least 283 mseconds. The third ALC feed back loop 310, therefore, does not distort the applied correlation signal (a), but, rather, maintains the peak value of the correlation signal at an almost constant level over time.

The voltage level (c) of correlation signal (a) at second hold capacitor 313 represents the peak voltage of the correlation signal (a). The time constant of the second hold capacitor 313 is sufficiently long for this capacitor 313 to hold this peak voltage (c) of the correlation signal (a). This peak voltage is used as a reference for detecting the location or position of a highest or fundamental peak occurring within a period of the correlation signal (a). Origin-point setting circuit 337 is used for this peak-locating purpose. The 100 Hz signal from frequency divider 333 causes switches S2 and S3 to be "on" for a short period during which time the voltage value of second hold capacitor 313 is transferred into first hold capacitor 315 through voltage follower 311 and diode D4. Switch S3 causes first timer circuit 320 to be reset and to start a timing sequence, and also causes comparator 321 to go low thereby keeping Q2 "off" so as not to affect the charge-up sequence of first hold capacitor 315. At the end of the timing sequence, the output of comparator 321 (f) goes high, putting Q2 "on". First hold capacitor 315 now begins to be discharged, as shown by curve (b) of FIG. 5B, at times $t_1$ and $T_3$. The source of Q2 is kept at a certain divided voltage, about 70–85% of the held voltage of second hold capacitor 313, and the first hold capacitor 315 is not discharged less than this divided voltage. If the first hold capacitor 315 were continuously discharged, errors would sometimes result in detecting a fundamental peak.

The charge up sequence of capacitor 315 begins again, for example at time $t_2$, when a voltage level of the correlation signal greater than the divided voltage is encountered. When the charge up sequence begins, the charge up current causes the current polarity detector 317 to produce a negative-voltage-charge-up-sequence signal (d) which turns Q1 "on". Q1, in turn, re-starts the timer circuit 320 which turns Q2 off and maintains the charge-up and hold sequence of first hold capacitor 315 undisturbed.

First timer 320 may be started and restarted by transistor Q1 as well as by switch S3 as shown by curve (e) of FIG. 5B.

The end of the charge up sequence corresponds to the location of a fundamental or primary peak within a 10 mseconds segment of the correlation signal (a). The location of a fundamental peak is marked approximately 1 msecond after actual occurrence of the peak. Time marker $t_3$ of waveform (f), for example, occurs approximately 1 msecond after fundamental peak (q). This time marker $t_3$, and time marker $t_1$, represent a change of state of first timer circuit 320 to a non-timing state. Time marker $t_2$ represents the return of first timer circuit 320 to a timing state. The output signal (f) from timer circuit 320 is shaped into a narrow pulse signal (g) by monostable multivibrator 323, and applied to AND gate 327. The period between the pulses occurring at times $t_1$ and $t_3$ of signal (g) represents the period of input signal (a). Signal period is therefore shown to be measured from an origin pulse at position $t_1$ to a period-marker pulse at position $t_3$ and not directly from peak to peak of the fetal input signal. Signal (g) is then converted by AND gate 327 to signal (n) and applied to converter 40 via output terminal 329. Signal (n) represents signal (g) having the period-marker pulse at time $t_3$ synchronized to clock pulse (k), i.e., occurring at a fixed location relative to clock pulse (k).

The trailing edge of output pulse (g) causes the set-reset flip-flop 325 to be set, inhibiting AND gate 327, thereby suppressing the output of later pulses (g) after time $t_4$. As shown by diagrams (f), (h), and (j) of FIG. 5B, the set-reset flip-flop 325 is re-set a short time after a fundamental peak is located; this short time is determined by second timer 330. The charge-up sequence signal (d) that is output from current polarity detector 317 is applied to signal conversion circuit 319, the output of which shown as waveform (m) of FIG. 5B, is applied to terminal 318.

Figure 6:
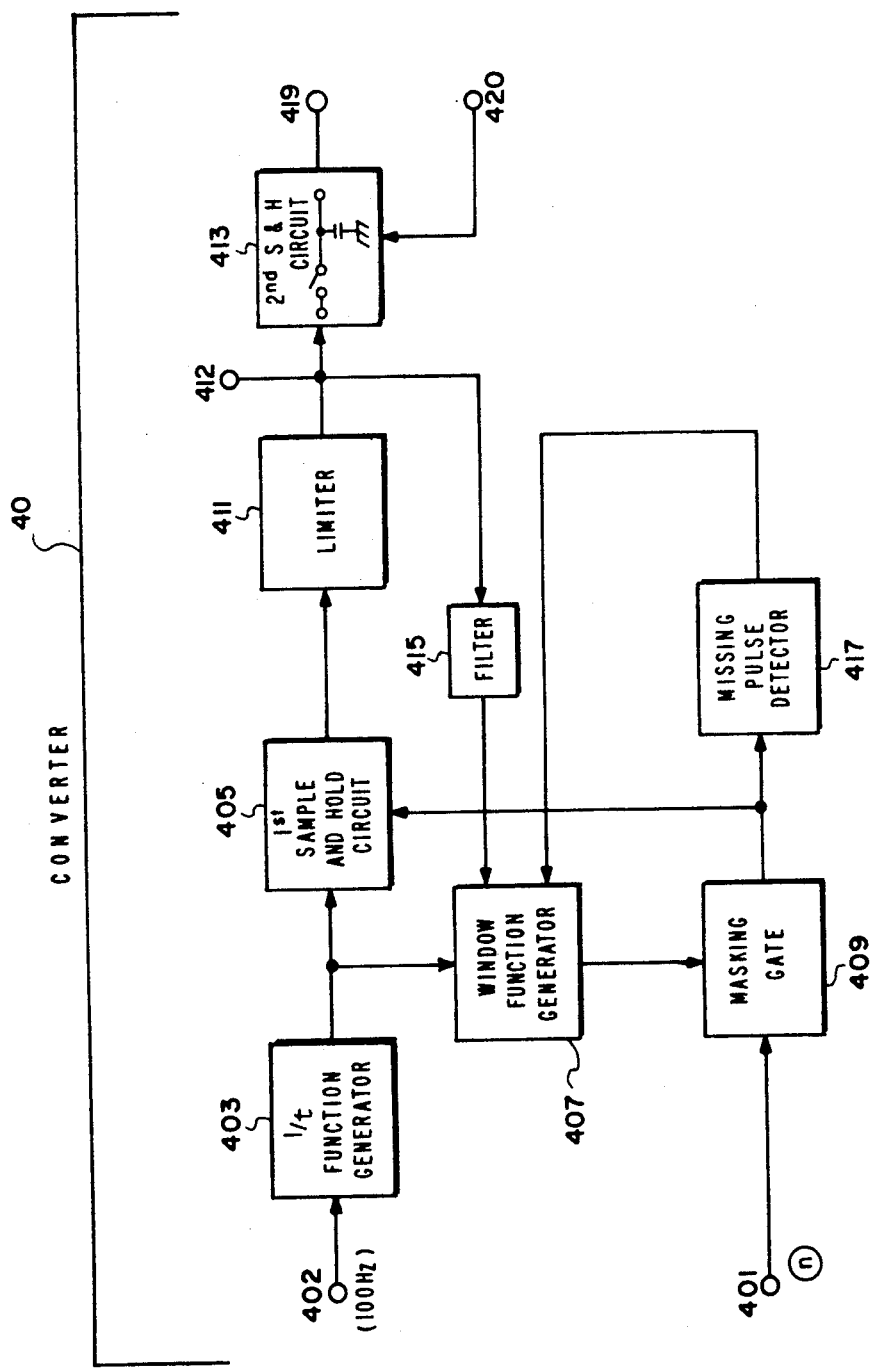
FIG. 6 is a block diagram illustrating the components of the converter of FIG. 1.
Figure 7:
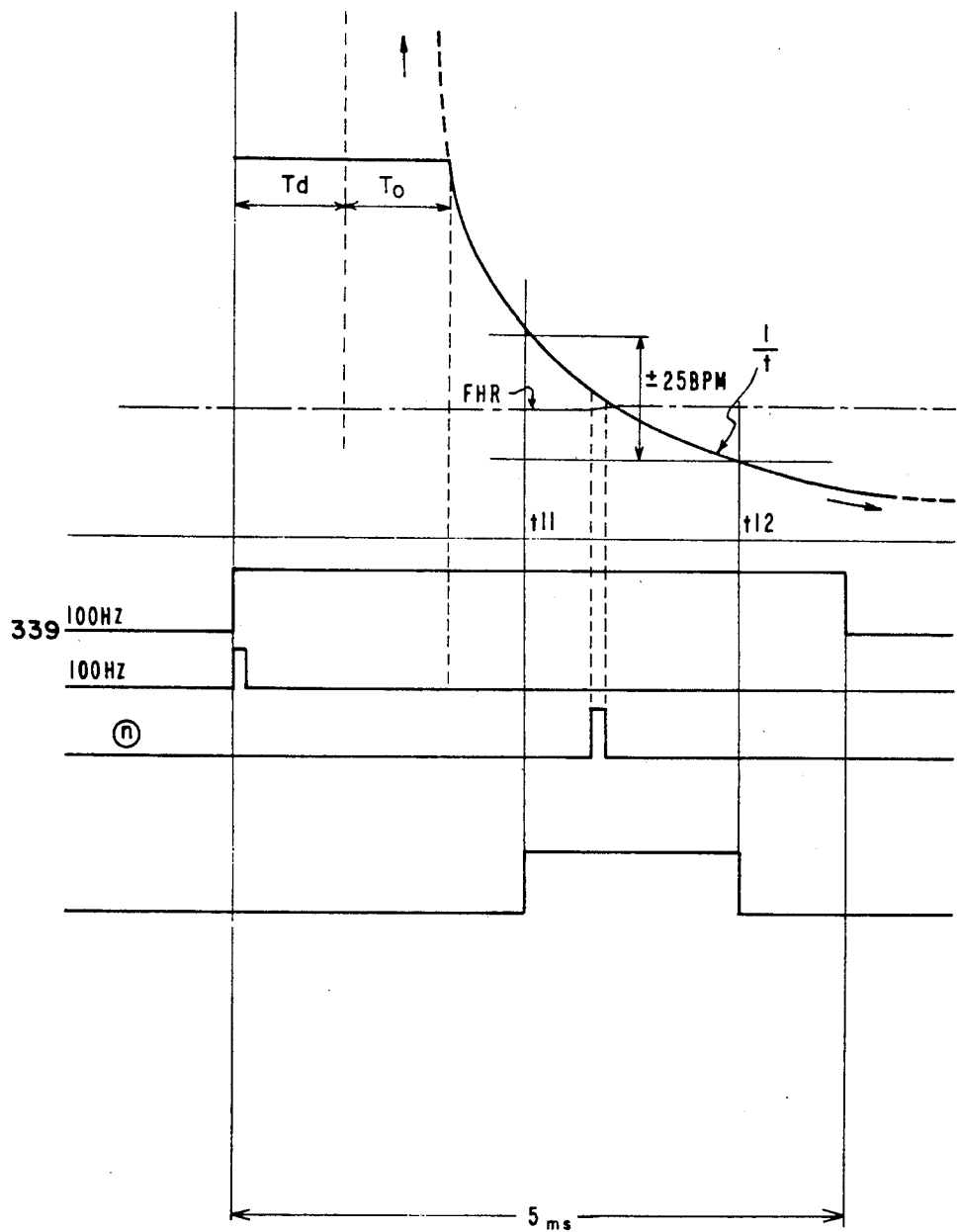
FIG. 7 is a combined waveform and timing diagram illustrating a method for deriving frequency values.

FIG. 6 shows period-to-fetal-heart-rate converter 40 in greater detail. Function generator 403 generates a $1/t$ function as shown in FIG. 7 coincident with the 100 Hz timing pulse applied to its terminal 402 from terminal 339 of peak detector 30. This $1/t$ function is a frequency function corresponding to different time differences or periods. Generation of the function $1/t$ starts $T_d + T_o$ time units after the occurrence of the leading edge of the 100 Hz pulse from terminal 339. $T_d$ is the time delay caused by first timer circuit 320 of peak detector 30. $T_o$ is a time period during which generation of the function $1/t$ is delayed so as to prevent the generation of too large a function value when $t$ is close to zero. Frequency or heart rate is determined from the ordinate of the function $1/t$ corresponding to the abscissa represented by the period-marker pulse (n). Before the period-marker pulse is used, however, it is checked to determine if it falls within an acceptable range or window. This checking is done by masking gate 409 and window function generator 407. Window function generator 407 generates a time domain window equivalent to a pulse having a frequency within ±25 beats per minute of a previously derived heart rate. The boundaries $t_{11}$ and $t_{12}$ of this window are shown in FIG. 7. If the period-marker pulse does not occur within this window, in which case the output of masking gate 409 is zero, the width of the window is increased by missing pulse detector 417. When a period-marker pulse does occur within the window, output from masking gate 407 causes circuit 405 to sample and hold the value of the function $1/t$ corresponding to the location or abscissa value of the period-marker pulse. If the period-marker pulse still does not occur within the increased window, a previously derived heart rate value, held by circuit 405, is used. First sample and hold circuit 405 samples and holds the value of the $1/t$ function corresponding to the location of the period-marker pulse. The output of circuit 405 is applied to limiter circuit 411 which limits output to a frequency value within 50–210 beats per minute, which is within the range of a typical recording or display device. The output of limiter circuit 411 is applied to terminal 412, to second sample and hold circuit 413, and to low pass filter 415. Low pass filter 415 filters this input signal and applies the filtered signal to window function generator 407 which stabilizes converter 40 operation.

Figure 8:
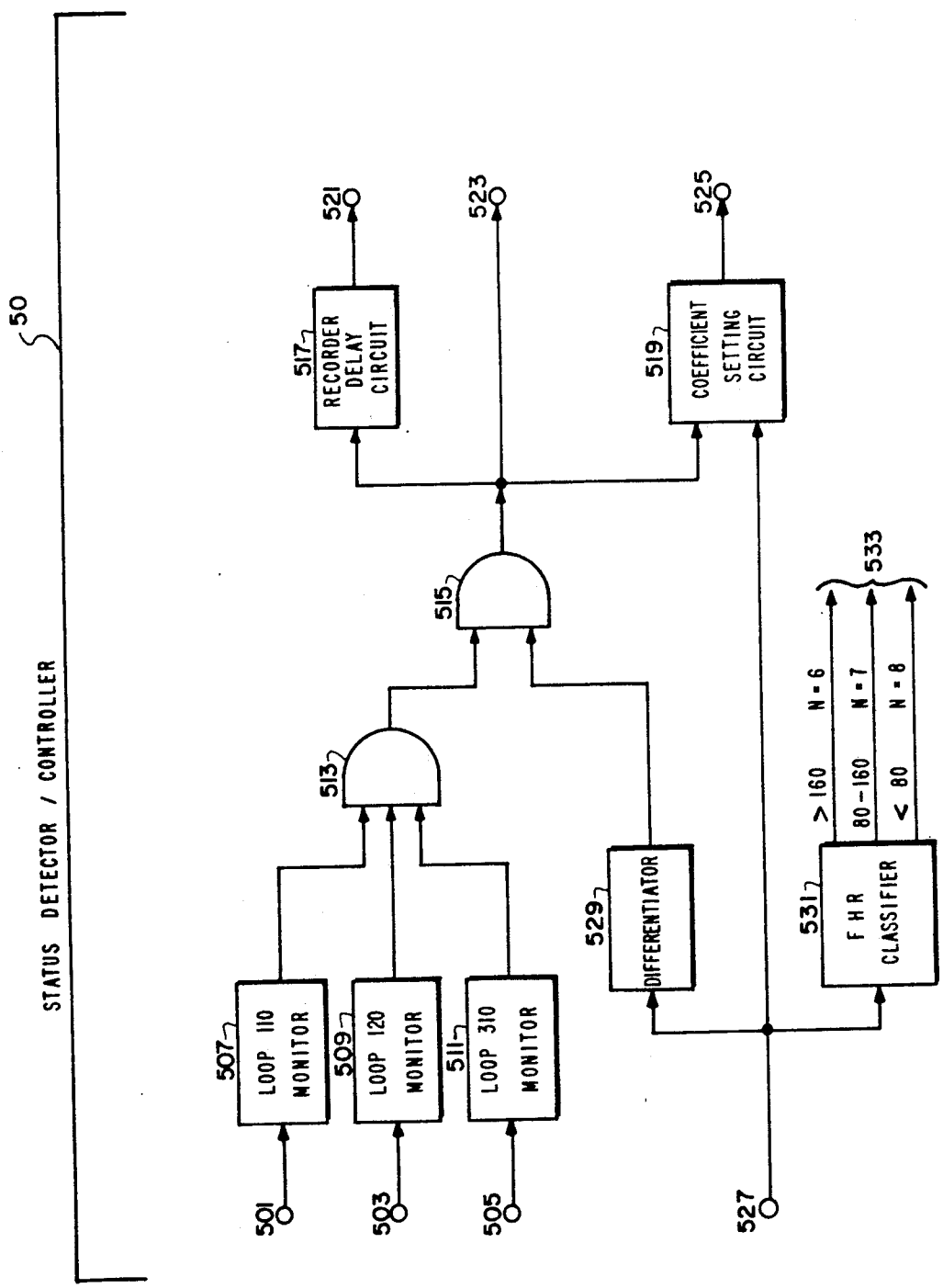
FIG. 8 is a combined block and logic diagram illustrating the components of the status detector/controller of FIG. 1.

The output from limiter circuit 411 to circuit 413 is sampled and held by circuit 413 only when an appropriate signal is received from status detector/controller 50 via terminal 420. Status detector/controller 50, shown in detail in FIG. 8, detects signal levels and operating status of the pre-processor 10, correlator 20, peak detector 30, and converter 40, optimizes the operations of these circuit elements, prevents the recording or displays of erroneous data, and starts and restarts the system.

By means of monitors 507, 509, and 511, signal levels applied to input terminals 501, 503, and 505, from terminals 114 and 126 (FIG. 2), and from terminal 312 (FIG. 4), are checked against predetermined values. If these input signal levels are satisfactory, logic one signals are applied by monitors 507, 509, 511 to AND gate 513, and a logic one signal level is produced by AND gate 513. Similarly, the heart rate signal applied to terminal 527 from terminal 412 (FIG. 6) is input to differentiator 529 which differentiates input signal and compares it with a predetermined value to determine the extent of change between the input signal and the predetermined value. If this change is satisfactorily small, a logic one level is produced by differentiator 529.

If all checks are satisfactory, logic one signals from AND gate 513 and from differentiator 529 are applied to AND gate 515, the output of which is applied via terminals 523 and 420 (FIG. 6) to sample and hold circuit 413 (FIG. 6). When such an output signal is applied to terminal 420, circuit 413 samples and holds the output heart rate signal from limiter circuit 411 and applies this newly sampled heart rate value via terminal 419 to display unit 6 and to recorder unit 7. When no signal is applied to terminal 420, circuit 413 does not accept a new signal value from limiter circuit 411, but transfers via terminal 419 its previously held heart rate value.

The output signal from AND gate 515 is also used in conjunction with delay element 517 to start and stop the recorder 7 and to raise and lower its stylus, thereby suppressing any erroneous trace. Delay element 517 prevents the frequent raising and lowering of the recorder's stylus, thereby preventing mechanical fatigue that can easily develop with frequent signal "dropouts".

The heart rate signal from terminal 412 (FIG. 6) is also applied to classifier 531, via terminal 527, for optimizing the variable N of correlator 20. Classifier 531 assigns to N the value 6, 7, or 8 depending on the value of the applied heart rate signal as follows:

| HEART RATE SIGNAL (beats per minute) | N |
|---|---|
| >160 | 6 |
| 80–160 | 7 |
| <80 | 8 |

The value assigned to N is output from classifier 531 via terminal 533 and applied to terminal 219 of multiplier 217 of correlator 20.

The output signal from AND gate 515 and the heart rate signal value applied to terminal 527 are used by coefficient setting circuit 519 to control the variable coefficient matrix or adding amplifier 119 in signal preprocessor 10 (FIG. 2).

Figure 9A:
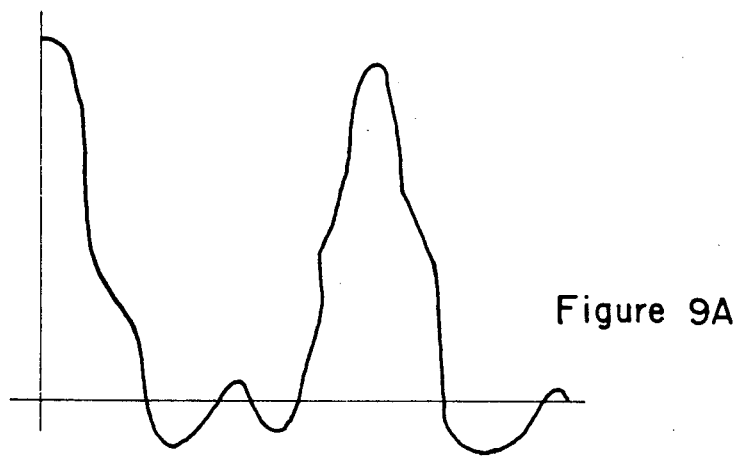
FIGS. 9A-9C are waveform diagrams illustrating output signals from the pre-processor of FIG. 1 with under-defined side peaks, over-defined side peaks, and adequately-defined side peaks.
Figure 9B:
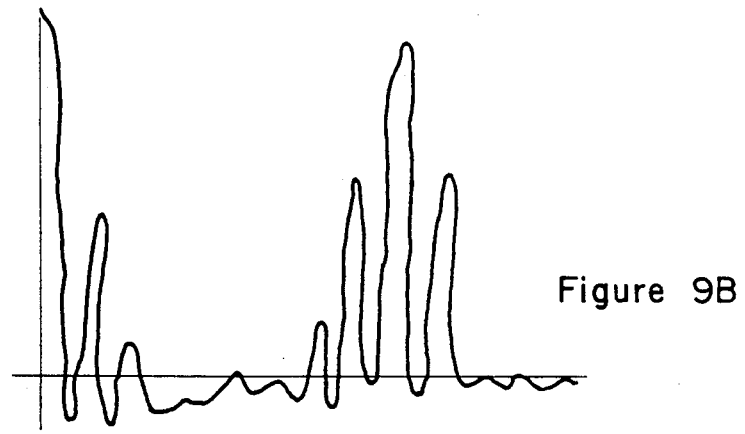
Figure 9C:
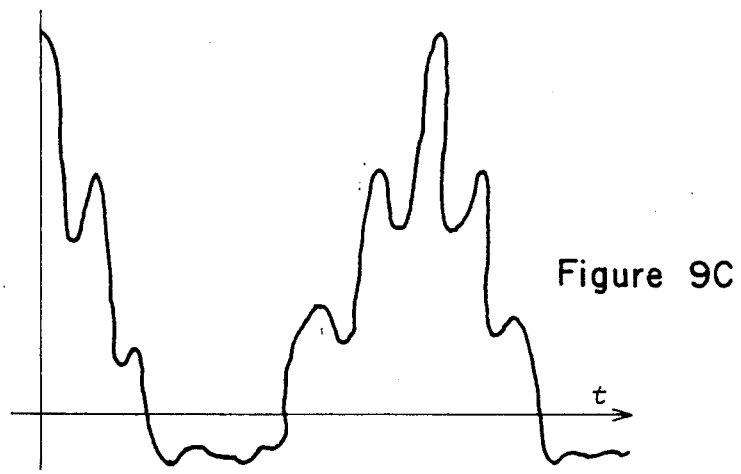
Figure 10:
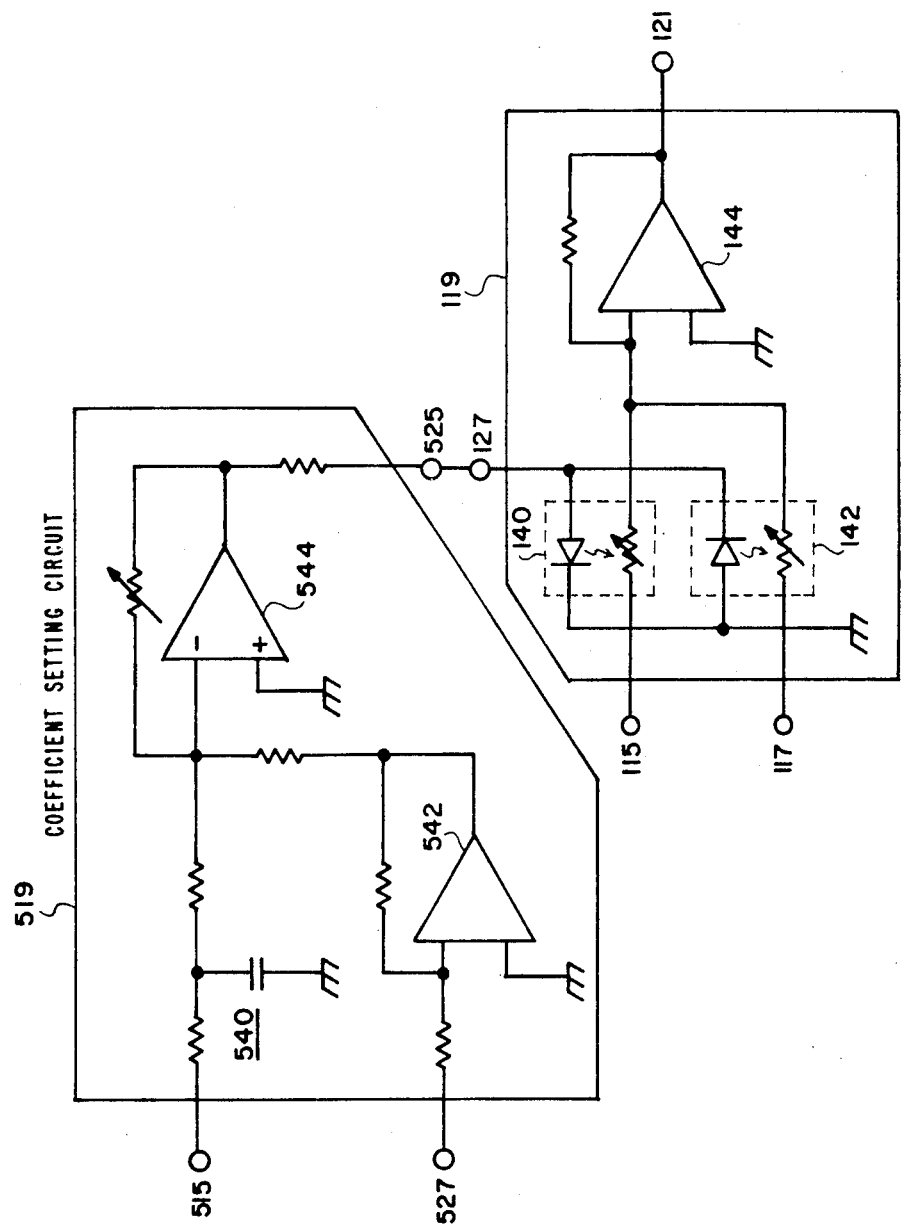
FIG. 10 is a schematic diagram illustrating a circuit component of the status detector/controller of FIG. 8 and a circuit component of the pre-processor of FIG. 2.

The output signal from circuit 519 is applied, via output terminal 525, to input terminal 127 of amplifier 119 (FIG. 2). This signal is used by amplifier 119 to control the mixing ration of the input signals from filters 115 and 117 to amplifier 119, such that the output of amplifier 119 is a waveform as shown in FIG. 9C, thereby minimizing the occurrence of side peaks as shown in FIG. 9B or insufficiently defined peaks as shown in FIG. 9A. FIG. 10 shows variable coefficient adding amplifier 119 and coefficient setting circuit 519 is greater detail. A frequent occurrence of zero-level signals from AND gate 515 to circuit 519, when detected by integrater circuit 540, causes circuit 119 to suppress the low frequency components of input signals from filters 115 and 117. An infrequent occurrence of zero-level signals from AND gate 515 to circuit 519 causes no changes in the mixing ratio of filters 115 and 117. In the case where signal condition is good, i.e., where signal levels are satisfactory and the heart rate does not change rapidly as indicated by small differences between successively derived heart rate values, the mixing ratio of low to high frequencies used by amplifier 119 may be, for example 15-20% when the heart rate is approximately 120 beats per minute. Heart rate signal from terminal 527 is applied to amplifier 542. The output of amplifier 542 is then combined with the output of integrator 540 and applied to the input of adding amplifier 544 which makes the peaks of the output signal from amplifier 119 more distinct by varying the widths of the peaks proportional to the heart rate signal. As the heart rate increases, these widths are decreased. The output from amplifier 544 drives oppositely connected LED photoconductive couplers 140 and 142, which produce variable coefficients or a mixing ratio for use by mixing amplifier 144. Input signals to these couplers 140 and 142 from filters 115 and 117 are mixed by amplifier 144 according to this mixing ratio. The output from amplifier 144 is applied to VGCA 121.

In addition to the preferred embodiment of the present invention described above, other versions may operate as follows:

1. A version may provide heart rate measurement only at the occurrence of a heart beat signal. Such a version may include a strobe or trigger pulse generator that applies a trigger pulse to sample and hold circuit 413 (FIG. 6) at the occurrence of each heart beat, thereby causing output information from circuit 413 to be displayed or recorded only at the time of occurrence of each heart beat;

2. A version may utilize a trigger or strobe pulse to reset or clear correlation register 223 (FIG. 3) each recirculation period, thereby obtaining a new correlation or heart rate value independent of previous correlations; and 3. A version may provide for selecting a value for N proportional to delay factor T and to apply this N value to multiplier 217 (FIG. 3) at terminal 219.

This invention is also applicable for determining instantaneous frequencies of other periodic signals upon the selection of appropriate signal level parameters, data length (generally equivalent to one period), and appropriate band pass filters 103 (FIG. 2). For example, appropriate filters may be:

| SOURCE SIGNAL | BAND PASS FILTER |
| --- | --- |
| Doppler | 300-1000 Hz |
| Fetal Phonocardiogram | 70-140 Hz |
| Fetal Electrocardiogram | 25-45 Hz |

I claim:
1. A system for measuring in real time by auto-correlation the frequency of a periodic input signal from a signal source, said system comprising:
   signal collection means coupled to the signal source for detecting and acquiring the periodic input signal;
   pre-processing means coupled to said signal collection means for mixing frequencies inherent in said periodic input signal to facilitate detection of reference peaks in said periodic input signal;
   correlator means coupled to said pre-processing means for producing within a selected duration of time equivalent to at least one period of said periodic signal a series of auto-correlation values representing an auto-correlation waveform with fundamental reference peaks;
   peak detector means coupled to said correlator means for detecting the locations of said fundamental reference peaks and for producing a period-marker pulse having a location relative to a predetermined clock pulse;
   converter means coupled to said peak detector means for deriving the frequency of the periodic input signal by converting to a frequency signal value the location of said period-marker pulse;
   display means coupled to said converter means for displaying frequency signal values from said converter;
   controller means coupled to said pre-processor means, correlator means, peak detector means, converter means, and display means for controlling the operations of all of said means, said controller means being effective for optimizing the production of auto-correlation waveform values utilizing the derived frequency of the periodic input signal.
2. A system as in claim 1 wherein:
   said pre-processing means includes means for filtering selected frequencies inherent in said periodic input signal.
3. A system as in claim 2 wherein:
   said correlator means includes an analog to digital converter for digitally sampling said periodic input signal at a predetermined sampling rate and producing a digital data sample each sampling period.
4. A system as in claim 3 wherein:
   said correlator means produces an auto-correlation value of the series during each sampling period by executing a predetermined number of calculation cycles during each sampling period utilizing at each subsequent calculation cycle the auto-correlation value calculated at an immediately previous cycle.
5. A system as in claim 4 wherein:
   said peak detector means includes a digital to analog converter for converting from digital to analog form auto-correlation waveform values received from said correlator.
6. A system as in claim 5 wherein:

said peak detector means, in producing said period-marker pulse, includes means for first producing an origin pulse within a predetermined delay period after a predetermined clock pulse, and means for producing a period-marker pulse relative to said origin pulse within a predetermined delay period after detecting a fundamental peak in said autocorrelation waveform;

said delay periods being effective for preventing detection of extraneous peaks bordering said fundamental peak.

7. A system as in claim 6 wherein:

said converter means includes means for deriving said frequency when said period-marker pulse occurs within a predetermined window period.

8. A system as in claim 7 wherein:

said controller means includes means for optimizing the frequency mixing operation of the pre-processor means utilizing the derived frequency of the periodic input signal.

9. A system as in claim 8 wherein:

said controller means further includes means for rejecting derived frequencies and for rederiving a frequency within the same sampling period within which the frequency was previously derived.

10. A system as in claim 9 further including recorder means coupled to said converter means and to said controller means for recording frequency signal values from said converter.

* * * * *